United States Patent
Pelc et al.

(10) Patent No.: US 7,860,210 B2
(45) Date of Patent: Dec. 28, 2010

(54) DATA NORMALIZATION IN INVERSE GEOMETRY COMPUTED TOMOGRAPHY SYSTEM

(75) Inventors: Norbert J. Pelc, Los Altos, CA (US); Jongduk Baek, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 76 days.

(21) Appl. No.: 12/273,223

(22) Filed: Nov. 18, 2008

(65) Prior Publication Data

US 2010/0124310 A1    May 20, 2010

(51) Int. Cl.
*A61B 6/00* (2006.01)
(52) U.S. Cl. .............................. 378/9; 378/4
(58) Field of Classification Search ............ 378/4, 378/9
See application file for complete search history.

(56) References Cited

U.S. PATENT DOCUMENTS

| | | | |
|---|---|---|---|
| 7,062,006 B1 | 6/2006 | Pelc et al. | |
| 7,072,436 B2 | 7/2006 | Pelc | |
| 2003/0108146 A1* | 6/2003 | Malamud | 378/19 |
| 2006/0018423 A1* | 1/2006 | Bruder et al. | 378/9 |
| 2006/0045235 A1* | 3/2006 | Bruder et al. | 378/9 |
| 2006/0210015 A1* | 9/2006 | Pelc et al. | 378/9 |
| 2007/0025499 A1* | 2/2007 | Bruder et al. | 378/9 |
| 2007/0280407 A1* | 12/2007 | Kunze et al. | 378/4 |

OTHER PUBLICATIONS

De man et al., Mulit-source inverse geometry CT: a new system concept for X-ray computed tomography, Medical Imaging, Proc of SPIE, vol. 6510, 2007, pp. 1-8.*
Schmidt et al., A three-dimensional reconstruction algorithm for an inverse-geometry volumetric CT system, Med Phys, 32, 11, Nov. 2005, pp. 3234-3245.*

* cited by examiner

*Primary Examiner*—Edward J Glick
*Assistant Examiner*—Alexander H Taningco
(74) *Attorney, Agent, or Firm*—Beyer Law Group LLP

(57) ABSTRACT

A method for imaging an object in a computed tomography (CT) system with a plurality of sources comprising a first source and a second source, wherein the plurality of sources together with a detector array are mounted on a rotatable gantry, and wherein an intensity of the second source has unknown fluctuations is provided. Projection data is collected using the first source in a first gantry position. Projection data is collected using the second source in a second gantry position, wherein projection data from the first source in the first gantry position substantially overlaps projection data from the second source in the second gantry position. Data from the first source at the first gantry position is used to correct for source fluctuations of the second source at the second gantry position.

19 Claims, 13 Drawing Sheets

DATA NORMALIZATION IN INVERSE GEOMETRY COMPUTED TOMOGRAPHY SYSTEM

STATEMENT REGARDING FEDERALLY SPONSORED RESEARCH OR DEVELOPMENT

This invention was made with Government support under contract EB 006837 awarded by the National Institutes of Health. The Government has certain rights in this invention.

BACKGROUND OF THE INVENTION

This invention relates generally to x-ray imaging including computed tomography (CT). More specifically the invention relates to a reconstruction algorithm for creating an inverse geometry CT image. Computed tomography (CT) is a medical technique for visualizing internal organs with high resolution. Both fan beams and cone beams of x-rays may be employed in CT.

SUMMARY OF THE INVENTION

In accordance with the invention, a method for imaging an object in a computed tomography (CT) system with a plurality of a first source and a second source, wherein the plurality of sources together with a detector array are mounted on a rotatable gantry, and of the second source has unknown fluctuations is provided. Projection data is collected using the first source in a first gantry position. Projection data is collected using the second source in a second gantry position, wherein some projection data from the first source in the first gantry position substantially overlaps projection data from the second source in the second gantry position. Data from the first source at the first gantry position is used to correct for source fluctuations of the second source at the second gantry position.

In another manifestation of the invention, a method for imaging an object in a computed tomography (CT) system comprising a plurality of sources and a detector array mounted on a rotatable gantry, wherein the plurality of sources comprise at least one source with a known intensity and at least one source with an intensity with an unknown fluctuation is provided. Projection data is collected from the plurality of sources in a first gantry position. The plurality of sources and a detector are rotated around the object to a second gantry position where projection data from the at least one source with known intensity in the first gantry position substantially overlaps with projection data from the at least one source with an unknown fluctuation. The overlapping projection data from one source is used to correct projection data from another source, and this step is repeated until all projection data that can be corrected.

In another manifestation of the invention, an inverse geometry computed tomography apparatus for performing computed tomography on an object is provided. A plurality of sources and a detector array are provided. The plurality of sources and detector array are mounted on a frame that allows the plurality of sources and detector array to be rotated around the object. A controller controls the frame, plurality of sources, and detector array. The controller comprises a display, at least one processor, and computer readable media. The computer readable media comprises computer readable code for collecting projection data using a first source of the plurality of sources in a first gantry position, computer readable code for collecting projection data using the second source at a second gantry position, wherein projection data from the first source in the first gantry position substantially overlaps projection data from the second source in the second gantry position, computer readable code for using data from the first source at the first gantry position to correct for source fluctuations of the second source at the second gantry position, computer readable code for generating a image using the corrected source fluctuations, and computer readable code for displaying the image on the display.

The invention and objects and features thereof will be more readily apparent from the following detailed description and appended claims when taken with the drawings.

DETAILED DESCRIPTION OF ILLUSTRATED EMBODIMENTS

Figure 1:
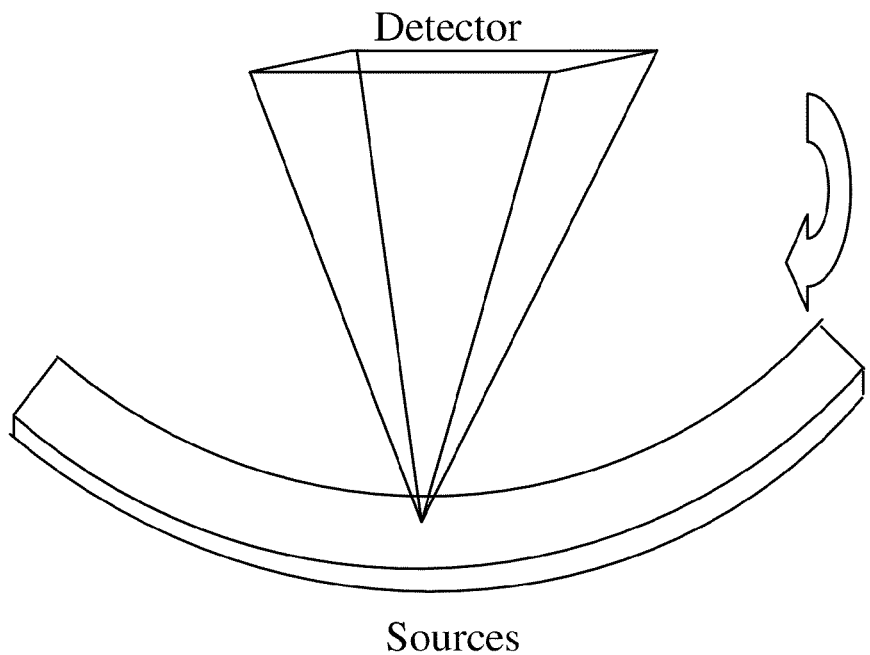
FIG. 1 shows the geometry of a multi-source IGCT system.

An inverse-geometry volumetric CT (IGCT) system uses a source array that is wide in the lateral or transverse direction opposite a narrower detector array. Because the source and detector can have the same extent in the axial direction, the IGCT system can provide sufficient sampling, and therefore it can prevent cone beam artifacts. In the IGCT system, each X-ray source illuminates a small portion of FOV. During raw data acquisition, any x-ray source intensity fluctuations can cause artifacts, and must be corrected, a process generally called "normalization". Conventional CT scanners use a "reference channel" to correct for source fluctuations. The reference channel can be located at the end of the array of detectors that measure the projection data. If this reference channel is unobstructed by the object being imaged, fluctuations in the reference channel reading reflect fluctuations in the source intensity and can be used to correct the projection data for this effect. Because each source of the IGCT system illuminates a portion of the FOV, a reference channel at the edge of the detector elements used to measure projection data can be obstructed by the object. In general, one cannot expect that such a reference channel can provide useful normalization data except for the measurements made by the source elements at the ends of the source array. Reference channels can be located at other locations, such as between the source and the object, but this can be inconvenient.

Data from x-rays generated by each source can be mapped into the projection space. Viewed in projection space one can appreciate that there is an overlap region in the data generated by adjacent sources. As a result, substantially the same projection data can be generated from different sources at different gantry positions. In the IGCT system, at least one source can illuminate a reference channel located at the edge of the detector array, and therefore the data from this source can be easily normalized. This normalized projection data can be used to normalize the raw data of another source with which it shares an overlap region. By performing this normalization process sequentially, an embodiment of the invention can do intensity normalization for the data from all sources. To evaluate the normalization algorithm, single slice projection data for a centered cylindrical water phantom were simulated. 200 IGCT views over 360 degrees were used. During data acquisition, 10% source output fluctuations were introduced. In this embodiment, it was assumed that the fluctuation errors were the same in all views, a worst case scenario. Grid driven interpolation was used to resample the IGCT data into fan beam data. The resampled fan beam data were filtered and back projected. The reconstructed image shows the image artifacts that result from uncorrected fluctuations, seen more clearly in the central profile. After applying the proposed normalization algorithm, the image artifacts were removed.

A multi-source IGCT system consists of a small 2D detector array and a number of sources distributed in transverse direction. FIG. 1 shows the geometry of a multi-source IGCT system.

In the IGCT system, each source is activated individually and generates x-rays that produce data corresponding to a small portion of the field-of-view (FOV), and a full FOV reconstruction is produced by combining projection data from all sources. During data acquisition, x-ray source intensity could fluctuate, and this can cause image artifacts. One potential reason of the source intensity fluctuation is the instability in the current and/or voltage of the x-ray source. For example, when the current fluctuates sinusoidally, source output has a similar fluctuation.

Conventional CT systems can also suffer from errors caused by source fluctuations. In order to correct the fluctuation, a conventional CT system uses a "reference channel", generally located at the edge of the detector array that is used to normalize the data to correct for variations in the x-ray source intensity. In the IGCT system, all sources cannot illuminate a reference channel at the edge of the detector array because each source has a small FOV. Therefore, a new normalization algorithm for the IGCT system is necessary.

Below, a brief description of the multi-source IGCT geometry is illustrated. The image artifacts due to the source intensity variations will be discussed, and a new method for normalization will be presented. The normalization method is based on the overlap region between sources in projection space. The analysis will be performed for two cases: one in which samples of each source are exactly overlapped in the overlap region, and a realistic sample pattern for an IGCT system. Since normalization errors and quantum noise cause image noise, the noise levels of each component are compared.

System Geometry

A multi-source IGCT system uses a small detector and a number of focal spots. In a volumetric (i.e., 3D) IGCT scanner, the axial length of a detector is approximately the same as the source to avoid cone beam artifacts. FIG. 1 shows the geometry of the multi-source IGCT system. Each focal spot is collimated to illuminate the entire detector array, corresponding to small cone beam projection. The present invention will be described in the context of a single slice (i.e., 2D) scanner. It will be clear to one of ordinary skill in the art that the concept is equally useful in a full volumetric scanner.

In the IGCT system, the size of the detector in the transverse direction is relatively small compared to the source. The specifications of a sample embodiment are summarized in Table 1. The detector consists of 256 detector elements and the source has 40 focal spots in the transverse direction.

TABLE 1

| Specifications for the IGCT system | |
|---|---|
| Source-to-Center-Detector distance | 850 mm |
| Source-to-Isocenter distance | 450 mm |
| Source arc angle | 127.41 degrees |
| Source arc length | 1000.63 mm |
| Source angular x-spacing | 3.27 degrees |
| Source x-spacing | 25.66 mm |
| Source z-spacing | 50 mm |
| Focal spot width | 1 mm |
| Detector width | 0.5 mm |
| FOV(transverse) | 50 cm |
| Number of 'Superviews' | 291/360° |

Method

1) Normalization Algorithm

Figure 2:
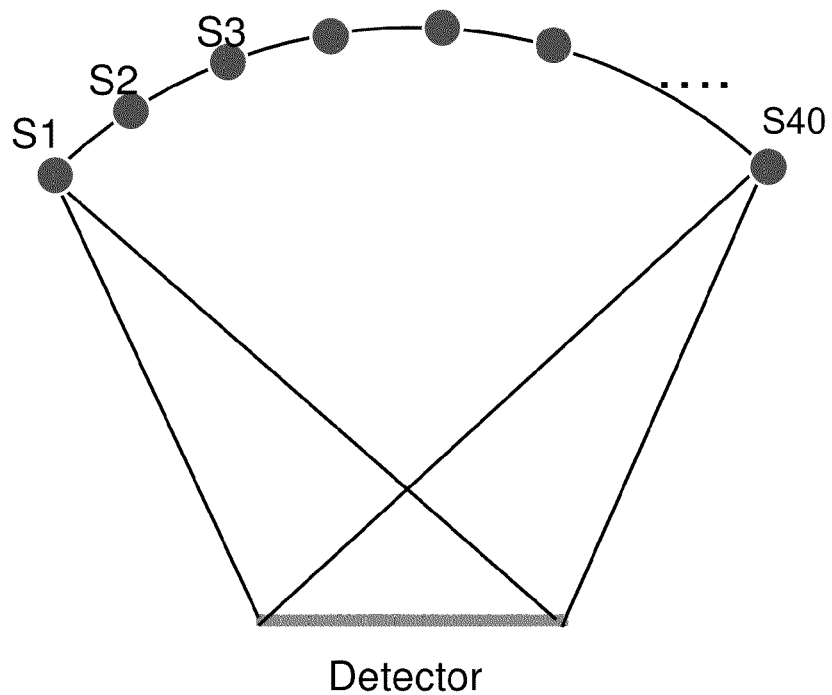
FIG. 2 is a schematic view of an IGCT system.

FIG. 2 is a schematic view of an IGCT system. As can be seen in FIG. 2, the IGCT system has multiple sources $S_1$ to $S_{40}$ and a small detector array. Each source emits an X-ray beam through a small portion of the field-of-view. Generally, the system acquires projection data during a 360-degree rotation of the sources and the detector array, although it is possible to produce images (and to use the current method) with rotations of less than 360 degrees, as is known in the art. During data acquisition, the intensity of each x-ray source can fluctuate, which can cause artifacts in the reconstructed image.

Figure 3A:
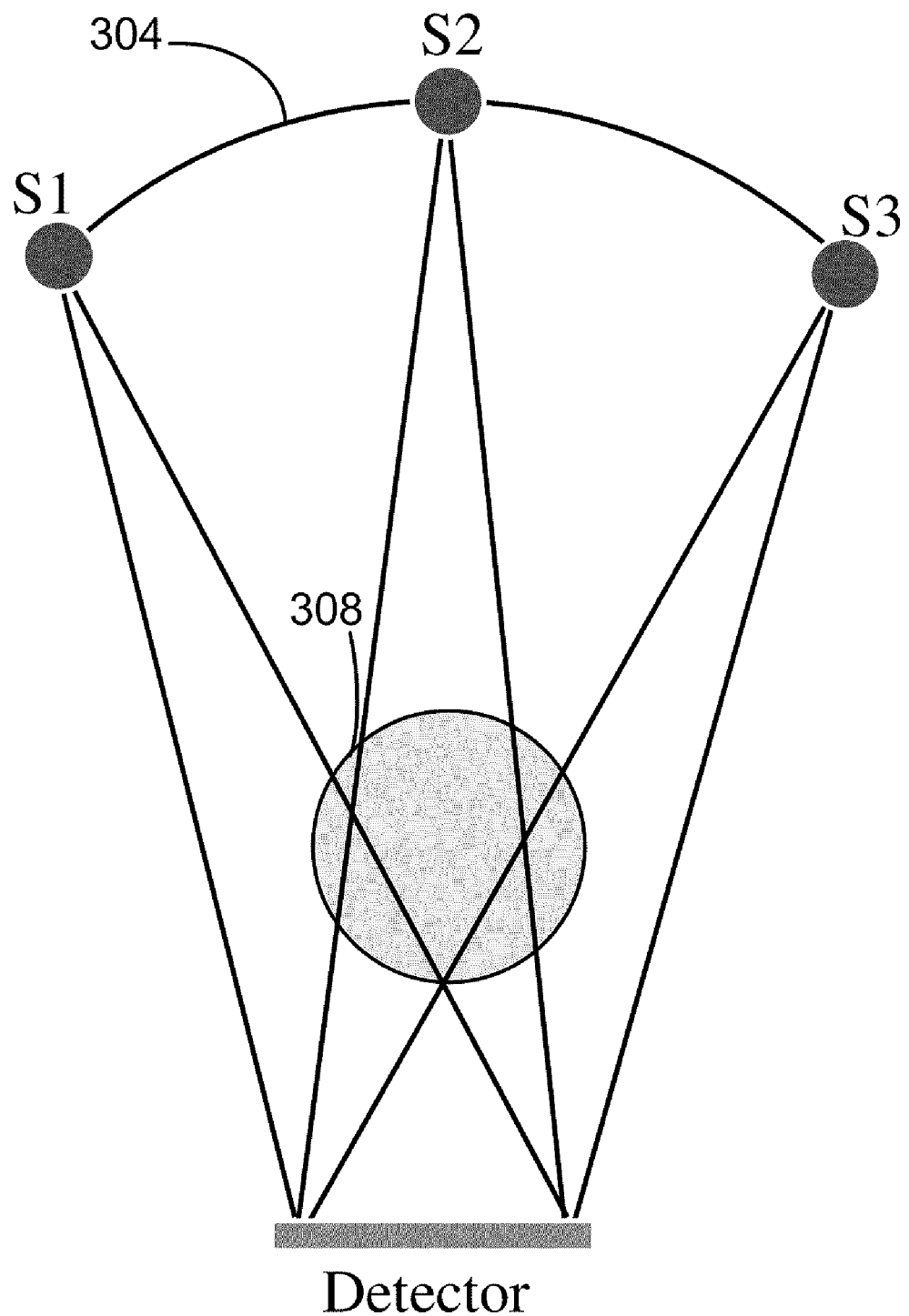
FIG. 3A shows each source of the IGCT system illuminates a portion of the FOV.

In conventional scanners, the system uses a "reference channel" to normalize the data, and this reference channel prevents image artifacts. The reference channel could be a single detector channel or the average of a number of reference detectors. The reference channel can be comprised of detector elements on either end of the CT detector array. However, in an IGCT system, since each source illuminates only a portion of the FOV, locating and illuminating the reference channels is difficult, as depicted in FIG. 3A. FIG. 3A shows a plurality of sources S1-S3 and a detector, which may be mounted on a frame 304 in such a way to form a gantry that allows the plurality of sources S1-S3 to be rotated around an object 308. In FIG. 3A, sources $S_1$ and $S_3$ may be able to direct x-rays along paths that do not cross the object and therefore reach reference channels, but source $S_2$ cannot. The conventional normalization methods are unable to correct for fluctuations in the output of source $S_2$.

Figure 3B:
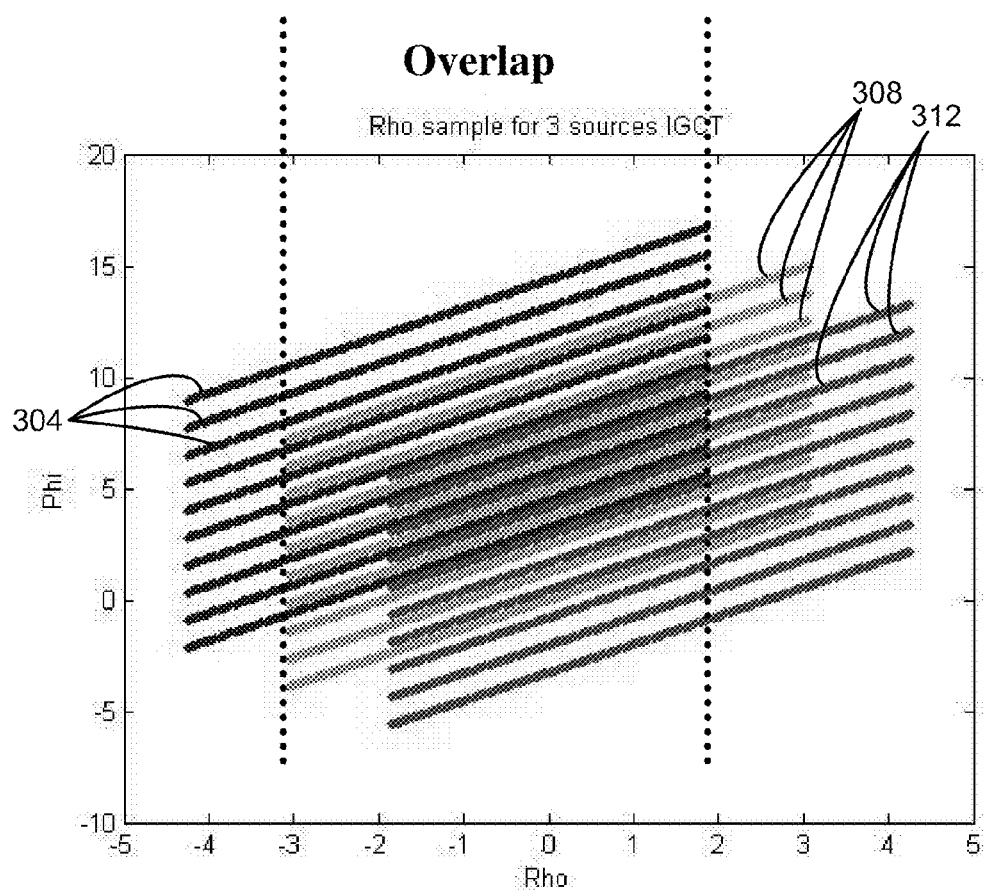
FIG. 3B shows the overlap region in the 2D Radon space for Rho samples of 3 sources of the IGCT system of FIG. 3A over 10 views.

This problem can be solved by using overlap regions illuminated by the sources. The geometry of the system is designed so that the radial distances of the rays from adjacent or nearby sources have some overlap. This is illustrated in FIG. 3B. Some of the rays produced by source $S_2$ will correspond to substantially the same ray paths as some of the rays from source $S_1$ at a different gantry position. FIG. 3B shows the location of samples in projection space for 3 sources of the IGCT system of FIG. 3A and for 10 views. The horizontal dimension in FIG. 3B, labeled Rho, is the signed radial distance of a ray path from the center of rotation. The vertical dimension, labeled Phi, is the angle of the ray relative to some reference direction (e.g., the y direction). Data samples 304 were measured using source $S_1$. The 10 roughly straight lines correspond to the measurements collected in 10 views. Samples 308 were measured using source $S_2$ and samples 312 were measured using source $S_3$. The first set of points 304, and the first set of points 308 and the first set of points 312 were all measured in the first IGCT view. The fact that each source contributes to measurements in different ranges in Rho can be appreciated in FIG. 3B and also in FIG. 3A. One can also appreciate an angular shift (downward in FIG. 3B) in the data from each of the sources. FIG. 3B also shows that the Rho values for the data from source $S_1$ overlap the Rho values for the data from source $S_2$. This is shown in FIG. 3B as the region between the two dotted lines. It can be appreciated that the data from source $S_2$ is substantially similar to that from source $S_1$ approximately 4 views later.

Let $N_0$ be the expected number of incident photons. For now, we assume this is the same for all sources. Let $\alpha_i$ be the intensity variation of source i in a particular view. Beer's law predicts that the number of detected photons, $N_i$, is:

$$N_i = \alpha_i N_0 e^{-\int u(x,y)ds} \quad (1)$$

where u(x,y) is an attenuation coefficient of the object.

Since the source $S_1$ sees the reference channel, $\alpha_1$ can be found from reference channel, and the raw data of source $S_1$ can be easily normalized. Because source $S_1$ and source $S_2$ have substantially the same rays in the overlap region, $\alpha_2$ can be estimated by using the following equation:

$$\frac{\alpha_2}{\alpha_1} = \frac{\sum_{j=1}^{m} N_{2,j}}{\sum_{j=n}^{m+n} N_{1,j}} \quad (2)$$

where, m is the number of the rho samples in the overlap region between sources $S_1$ and $S_2$.

Because $N_1$, $N_2$ and $\alpha_1$ are known, $\alpha_2$ can be estimated by using equation (2). This estimation process can be generalized for the 40 sources IGCT system. If the expected incident intensity is not the same for all the sources, Eq. 2 can be modified to include those expected values. There would be an additional multiplication on the right hand side by the ratio of expected incident intensities of source 1 over source 2.

However, as can be seen in FIG. 3B, rays from source $S_1$ are not exactly along the same paths as those from source $S_2$ in the overlap region. Interpolation can be used to estimate $\alpha_2$. In a preferred embodiment the adjacent 4 data points are used. The analysis will be presented in two steps. The first analysis is based on the case that rays from different sources are exactly overlapped in the overlap region. The second step is to apply the previous analysis to the 40 source IGCT system.

2) Exactly Overlapped Case

If source $S_1$ and source $S_2$ have n rays in the overlap region, $\alpha_2$ can be estimated by the following equation:

$$\log(\hat{\alpha}_2) = \frac{\sum_{i=1}^{n} \log(N_{2,i}) - \sum_{j=1}^{n} \log(N_{1,j})}{n} + \log(\alpha_1) \quad (3)$$

where $N_{1,j}$ and $N_{2,i}$ are the detected number of photons of source $S_1$ and source $S_2$ at the ith and jth detector channel.

This estimation process can be generalized by the following equation:

$$\log(\hat{\alpha}_{m+1}) = \frac{\sum_{i=1}^{n} \log(N_{m+1,i}) - \sum_{j=1}^{n} \log(N_{m,j})}{n} + \log(\hat{\alpha}_m) \quad (4)$$

In the noiseless case, equation (4) gives an exact estimation value. However, the CT data has noise, for example due to photon-counting statistics, and this causes an estimation error. This estimation error also propagates as the estimation process continues. For example, if we have an estimation error in $\log(\alpha_2)$, it affects the estimation of $\log(\alpha 3)$. One way to reduce an estimation error is to use as many overlap regions as possible. For example, in estimating $\log(\alpha_3)$, the overlap region between source $S_1$ and source $S_3$ can also be used. From the overlap region between sources $S_1$ and $S_3$, and between sources $S_2$ and $S_3$, $\log(\alpha_3)$ can be estimated separately, and then averaged. However, a more optimal way is to use weighting factors $w_1$ and $w_2$, so that the estimation variance of $\log(\alpha_3)$ is minimized. This estimation process can be expressed $$\log(\hat{\alpha}_3) = w_1 \left[ \frac{\sum_{i=1}^{n_{3,2}} \log(N_{3,i}) - \sum_{j=1}^{n_{3,2}} \log(N_{2,j})}{n_{3,2}} + \log(\hat{\alpha}_2) \right] + w_2 \left[ \frac{\sum_{i=1}^{n_{3,1}} \log(N_{3,i}) - \sum_{j=1}^{n_{3,1}} \log(N_{1,j})}{n_{3,1}} + \log(\hat{\alpha}_1) \right] \quad (5)$$

let $$X = \frac{\sum_{i=1}^{n_{3,2}} \log(N_{3,i}) - \sum_{j=1}^{n_{3,2}} \log(N_{2,j})}{n_{3,2}} + \log(\hat{\alpha}_2),$$

$$Y = \frac{\sum_{i=1}^{n_{3,1}} \log(N_{3,i}) - \sum_{j=1}^{n_{3,1}} \log(N_{1,j})}{n_{3,1}} + \log(\hat{\alpha}_1)$$

-continued then $$\begin{bmatrix} w_1 \\ w_2 \end{bmatrix} = \begin{bmatrix} \text{COV}(X,Y) - \text{VAR}(X) & \text{VAR}(Y) - \text{COV}(X,Y) \\ 1 & 1 \end{bmatrix}^{-1} \begin{bmatrix} 0 \\ 1 \end{bmatrix} \quad (5)$$

where $n_{3,2}$ is a number of overlap channels between source $S_3$ and source $S_2$, $n_{3,1}$ is a number of overlap channels between source $S_3$ and source $S_1$. If there is another overlap region between source $S_4$ and source $S_1$, three weighting factors are introduced.

After the estimation process, the variance of a reconstructed CT image depends on photon-counting statistics and the estimation error of $\log(\alpha_i)$. If we take the log of equation (1), we have the following expression:

$$P(x) = \int u(x,y) ds = \log(N_0) - \log(N_i) + \log(\alpha_i) \quad (6)$$

After estimating $\log(\alpha)$, equation (6) is expressed as:

$$\hat{P}(x) = \int u(x,y) ds = \log(N_0) - \log(N_i) + \log(\alpha_i) - \log(\hat{\alpha}_i) \quad (7)$$

From equation (7), the estimation error of $\log(\alpha)$ is expressed as:

$$\text{Estimation\_error} = \log(\alpha_i) - \log(\hat{\alpha}_i) \quad (8)$$

We will now analyze the effect of estimation errors in the CT image. A fan beam system has the following reconstruction formula:

$$f(x,y) = \frac{2\pi \times \tau}{ML^2} \sum_{i=1}^{M} \sum_{k} w \hat{P}_i(k\tau) h(k\cos\theta_i + y\sin\theta_i - k\tau) \quad (9)$$

where M is the total number of views, $\tau$ is a sampling distance, L is a magnification factor from the reconstructed point to the detector, w is a cosine weighting factor determined by the angle between the incident ray and the normal of the detector surface, and h is a filter coefficient.

By inserting equation (7) into equation (9), the variance equation of the reconstructed image is derived as:

$$\text{Var}[f(x,y)] = \quad (10)$$

$$\left(\frac{2\pi \times \tau}{ML^2}\right)^2 \sum_{i=1}^{M} \sum_{k} w^2 \left[\frac{1}{N_i} + \text{Var}(\log(\hat{\alpha}_i))\right] h^2(k\cos\theta_i + y\sin\theta_i - k\tau)$$

Figure 4:
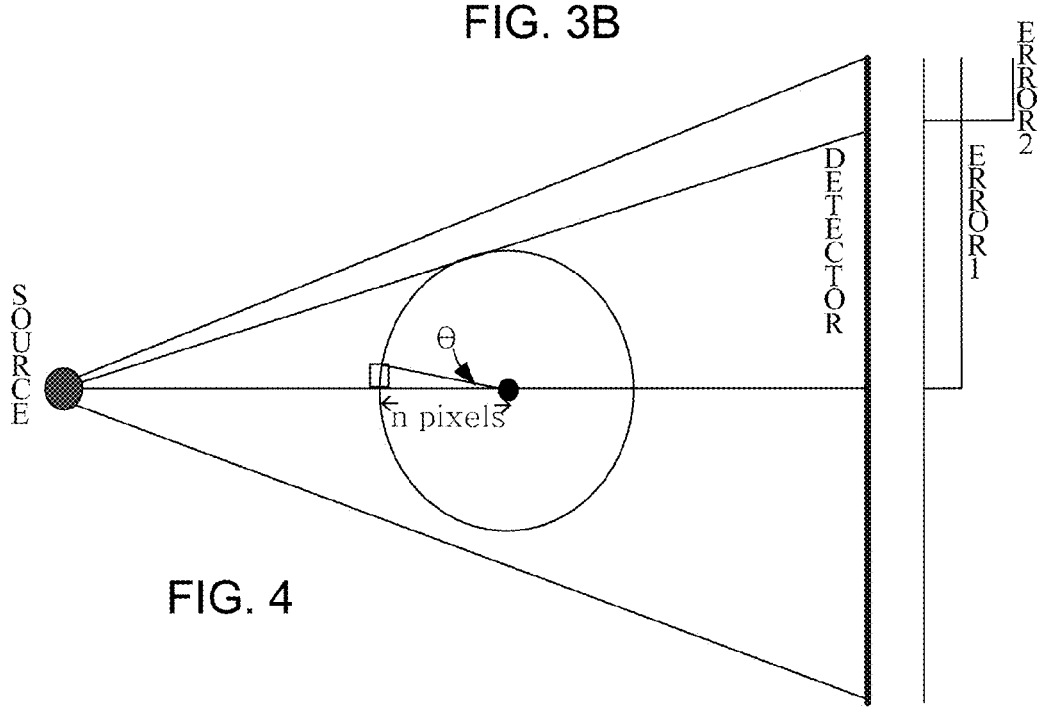
FIG. 4 shows a piecewise constant estimation error.

This expression shows the effect of each noise component in the reconstructed image. Equation (10) holds only when each noise component is independent from channel to channel, which is true for photon-counting statistics. However, the estimation error of $\log(\alpha)$ is piecewise constant. We analyze this effect using a fan beam geometry in which there is an additional error that is piecewise constant across the fan beam. FIG. 4 shows this piecewise constant error, which models the effect of source intensity estimation errors. Because the variance is proportional to the number of rays passing through a pixel, a new variance equation for the estimation error can be derived. If M views were used, the angle increment is $2\pi/M$. In order to find a variance of a pixel at a radial distance, r, from the isocenter, the angle $\theta$ in FIG. 4 is expressed as:

$$\theta = \tan^{-1} \frac{\text{pixel\_distance}}{n \times \text{pixel\_distance}} = \tan^{-1} \frac{1}{n} \quad (11)$$

By dividing this angle with the angle increment, $2\pi/M$, the relative ratio of rays passing through a pixel can be calculated. After multiplying this ratio to the second component (that is, variance due to the estimation error) of equation (10), a new variance equation of the estimation error can be derived as $$\text{New\_Var}[f(x,y)] = \left(\frac{2\pi \times \tau}{ML^2}\right)^2 \sum_{i=1}^{M} \sum_{k} w^2 \text{Var}(\log(\hat{\alpha}_i)) \quad (12)$$

$$h^2(k\cos\theta_i + y\sin\theta_i - k\tau) \times \frac{M}{2\pi} \tan^{-1} \frac{1}{n}$$

$$= \frac{2\pi\tau^2}{ML^4} \tan^{-1}\frac{1}{n} \times \sum_{i=1}^{M} \sum_{k} w^2 \text{Var}(\log(\hat{\alpha}_i))$$

$$h^2(k\cos\theta_i + y\sin\theta_i - k\tau)$$

Equation (12) holds for $n \geq 1$. For $n=0$, the expression of the new variance is the same as that of the original variance equation. One should appreciate that errors at a particular radial distance only affect pixels with larger radial distances. For example, the error region labeled error 2 in FIG. 4 does not affect the variance inside the circle. The variance due to error 2 for pixels outside the circle follows equation (12). The variance on the circle is two times higher than equation (12) because the number of rays passing through a pixel on the circle is half of the original number of rays.

In order to examine the effect of the estimation error compared to that of the photon-counting statistics, a noise variance ratio between the photon-counting statistics and the $\log(\alpha)$ estimation error can be calculated. Because each variance equation can be decomposed separately by using equation (10) and (12), the variance ratio can be expressed as:

$$\text{Variance\_ratio} = \quad (13)$$

$$\frac{2\pi}{M} \times \frac{\sum_{i=1}^{M} \sum_{k} \frac{1}{N_i} h^2(k\cos\theta_i + y\sin\theta_i - k\tau)}{\sum_{i=1}^{M} \sum_{k} \text{Var}(\log(\hat{\alpha}_i)) h^2(k\cos\theta_i + y\sin\theta_i - k\tau) \times \tan^{-1}\frac{1}{n}}$$

3) Analysis of the IGCT Geometry

Figure 5:
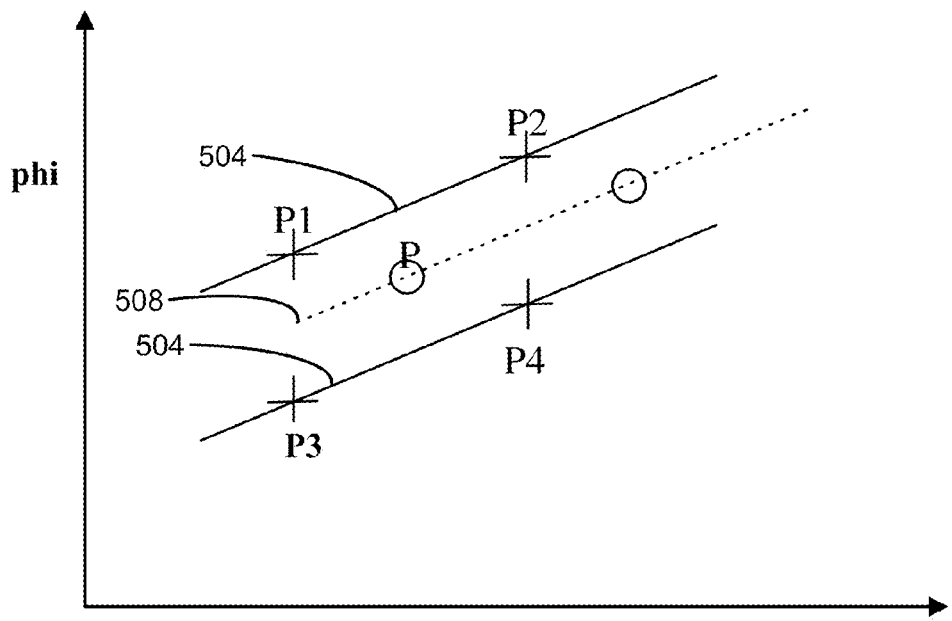
FIG. 5 is a plot of phi verses rho samples for source $S_1$ and source $S_2$.

FIG. 5 is a plot of phi verses rho and shows the samples for source $S_1$ and source $S_2$, where the solid lines 504 are for source $S_1$ and the dotted line 508 are for source $S_2$. As can be seen in FIG. 5, the rays of source $S_1$ are not exactly overlapped with the rays of source $S_2$ in the overlap region. Therefore, the estimation of $\log(\alpha)$ is performed by using interpolation in projection space. By using equation (6), each projection data in FIG. 5 is expressed as $$P_1 = \log(N_0) - \log(N_1) + \log(\alpha_1)$$

$$P_2 = \log(N_0) - \log(N_2) + \log(\alpha_1)$$

$$P_3 = \log(N_0) - \log(N_3) + \log(\alpha_2)$$

$$P_4 = \log(N_0) - \log(N_4) + \log(\alpha_2)$$

$$P = \log(N_0) - \log(N) + \log(\alpha) \quad (14)$$

where $\log(\alpha_1)$ and $\log(\alpha_2)$ are the intensity variations of source $S_1$ at the 1st view and 2nd view. Because source $S_1$ can be monitored with a reference channel, $\log(\alpha_1)$ and $\log(\alpha_2)$ are known. By using $P_1$, $P_2$, $P_3$ and $P_4$, the projection value of P can be estimated by the following equation:

$$\hat{P} = w_1 P_1 + w_2 P_2 + w_3 P_3 + w_4 P_4 \quad w1+w2+w3+w4=1 \quad (15)$$

If we assume $P \cong \hat{P}$ (that is, there is no interpolation error), the estimation of $\log(\alpha)$ is performed as:

$$\log(\hat{\alpha}) = \log(N) - w_1(\log N_1 - \log \alpha_1) - w_2(\log N_2 - \log \alpha_1) - w_3(\log N_3 - \log \alpha_2) - w_4(\log N_4 - \log \alpha_2) \quad (16)$$

This estimation process can be applied sequentially to all overlap channels.

Simulations

To examine the effect of the source intensity variation in the reconstructed image, noiseless projection data were simulated for a centered 5 cm cylinder. Projection data were produced by calculating the path length of a given ray through the cylinder. During the data acquisition, it is assumed that the source output fluctuates randomly within ±10%. Projection data of the IGCT system were rebinned into a fan beam, and filtered back projection was performed. For a noise simulation, we modeled quantum noise with 100 photons per ray, and intensity normalization was conducted. 291 superviews equally spaced over 360 degrees were used.

Result

1) Noiseless Reconstruction with Source Output Fluctuation

Figure 6A:
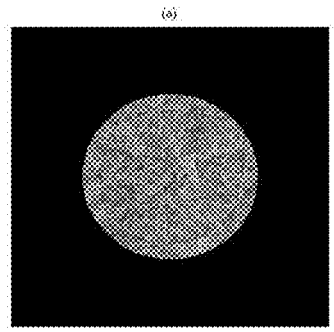
FIGS. 6A-B show reconstructed images of the centered water cylinder
Figure 6C:
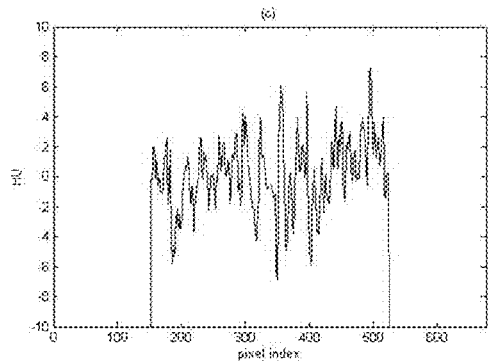
FIGS. 6C-D show the central profile through the reconstructed image.
Figure 6B:
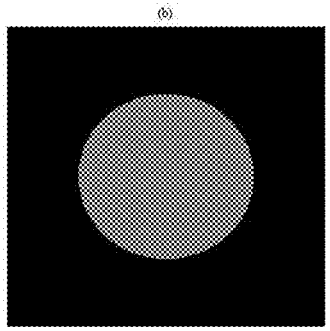
Figure 6D:
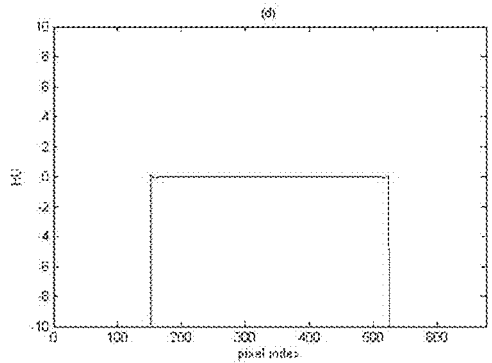

A cylinder object with a 10 cm diameter was used for the reconstruction. FIGS. 6A-B show reconstructed images of the centered water cylinder, where FIG. 6A shows the IGCT simulation without correction for source output fluctuation using $\log(\alpha)$ estimation, and FIG. 6B shows the IGCT simulation with correction using the $\log(\alpha)$ estimation. FIGS. 6C-D show the central profile through the reconstructed image, where FIG. 6C shows the IGCT simulation without $\log(\alpha)$ estimation, and FIG. 6D shows the IGCT simulation with $\log(\alpha)$ estimation.

FIG. 6A shows the reconstructed image with a source output fluctuation. The image is displayed with a window width of ±10 HU. FIG. 6C plots the central horizontal profile through the image. After estimating $\log(\alpha)$, the artifacts level is reduced to below 1 HU as shown in FIG. 6B and FIG. 6D.

2) Analysis of the Exactly Overlapped Case with Noise Data

Variance of the Estimation Error

Figure 7:
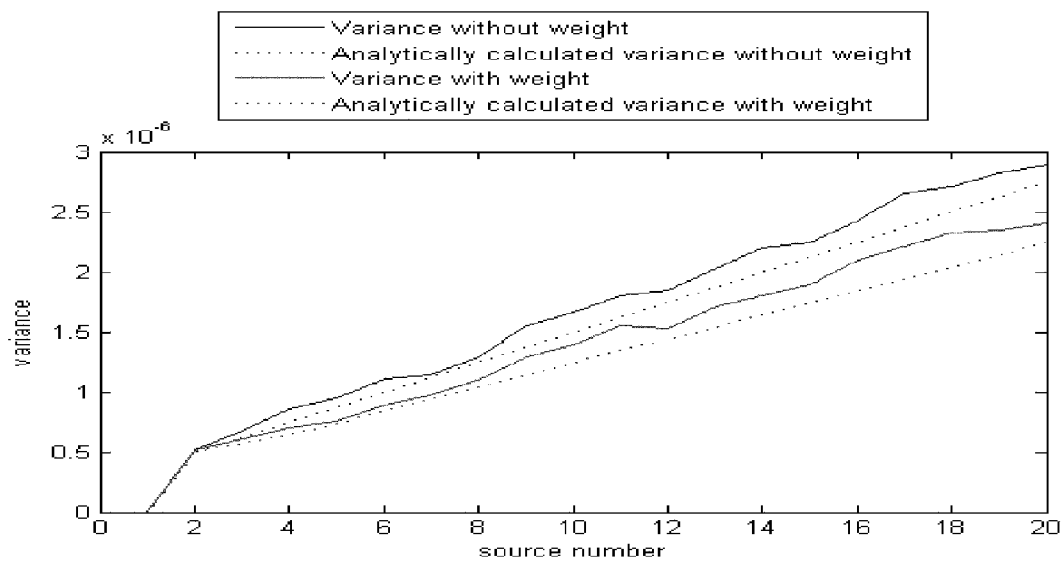
FIG. 7 is a variance graph of the estimation error with and without weighting.

The variance for estimating $\log(\alpha)$ was calculated by assuming a 250×250 element detector array in which that 200×250 rays are exactly overlapped between adjacent sources. Because source $S_1$ and source $S_{40}$ see the reference channel, the estimation process was performed symmetrically toward the center. Therefore, the variance calculation was performed from source $S_1$ to source $S_{20}$. The variance of the estimation error was also calculated when weighting factors were used as described in equation (5). FIG. 7 is a variance graph of the estimation error with and without weighting factors. As shown in FIG. 7, there is a 20% improvement of the estimation variance when weighting factors were used.

Figure 8A:
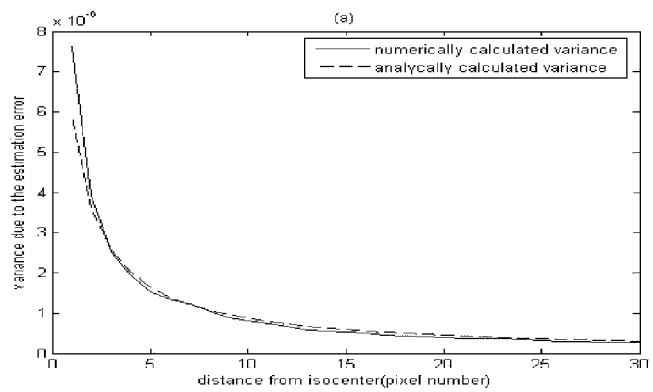
FIG. 8A shows the noise variance of the reconstructed image due to the estimation error.

Noise Variance Ratio Between Photon-Counting Statistics and the Estimation Error To examine the effect of the estimation error in the reconstructed image, we assume the estimation error of $\log(\alpha)$ has a discontinuity at the center channel as shown in FIG. 4. After reconstruction, the variance of the pixels at the same radial distance from isocenter is calculated as a function of radial distance from the isocenter. FIG. 8A shows the noise variance of the reconstructed image due to the estimation error. To calculate the variance ratio, the following steps were used.

By assuming no output fluctuation for any sources, the $\log(\alpha)$ estimation is performed. To simplify the calculation, weights were not used in the estimation of $\log(\alpha)$.

Acquire estimation error image by taking the difference between two reconstructed images with and without $\log(\alpha)$ estimation.

Calculate the variance of the pixels which have the same radial distance from the isocenter in the estimation error image and a noise reconstruction image without $\log(\alpha)$ estimation.

Calculate the variance ratio by using the calculated variance value in step (3).

Figure 8B:
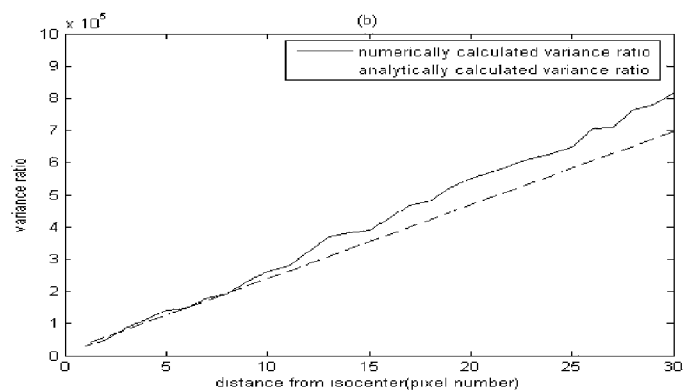
FIG. 8B shows the noise variance ratio between photon-counting statistics and estimation error in the reconstructed image.

FIG. 8B shows the noise variance ratio between photon-counting statistics and the estimation error in the reconstructed image from the simulation and also from the analytical calculation using equation (13). As can be appreciated in FIG. 8B, the minimum value of the variance ratio is more than 30,000. Therefore, the noise component due to the estimation error is negligible compared to the noise in the CT image from photon-counting statistics. The variance ratio will depend on the details of the application, but for the present example we can comfortably conclude that the correction method corrects for errors from source intensity fluctuation without introducing a significant amount of additional noise.

3) Analysis of the Multi-Source IGCT System

Variance of the Estimation Error in Multi Source IGCT System

Figure 9:
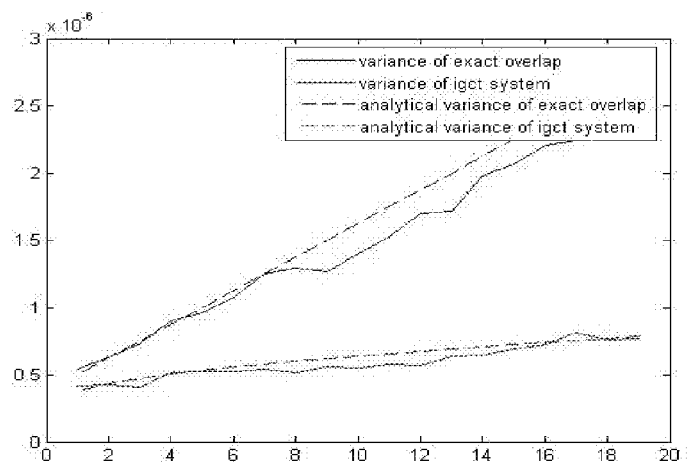
FIG. 9 is a graph showing the comparison of the estimation error between exactly overlapped case and the multi source IGCT system.

FIG. 9 is a graph showing the comparison of the estimation error between the exactly overlapped case and the multi source IGCT system. As can be seen in FIG. 9, the variance of the estimation error in the multi source IGCT system is much smaller than that of the exactly overlapped case. As illustrated in FIG. 5, bi-linear interpolation causes smoothing in estimating $\log(\alpha)$, and this reduces the variance of the $\log(\alpha)$ estimation. This result can be understood from a statistical point of view. For example, when the rho samples are exactly overlapped, only one rho sample line of source $S_1$ is used to estimate $\log(\alpha_2)$. In IGCT system, two rho sample lines of source $S_1$ are used to estimate $\log(\alpha_2)$. In estimating $\log(\alpha_3)$, three rho sample lines of source $S_1$, and two rho sample lines of source $S_2$ are used. Because more data samples are used to estimate $\log(\alpha)$ in the IGCT system, the variance of the estimation is smaller, and therefore the variance ratio in the IGCT system is much smaller than the exactly overlapped case Noise Reconstruction with Source Output Fluctuation in IGCT System.

Figure 10A:
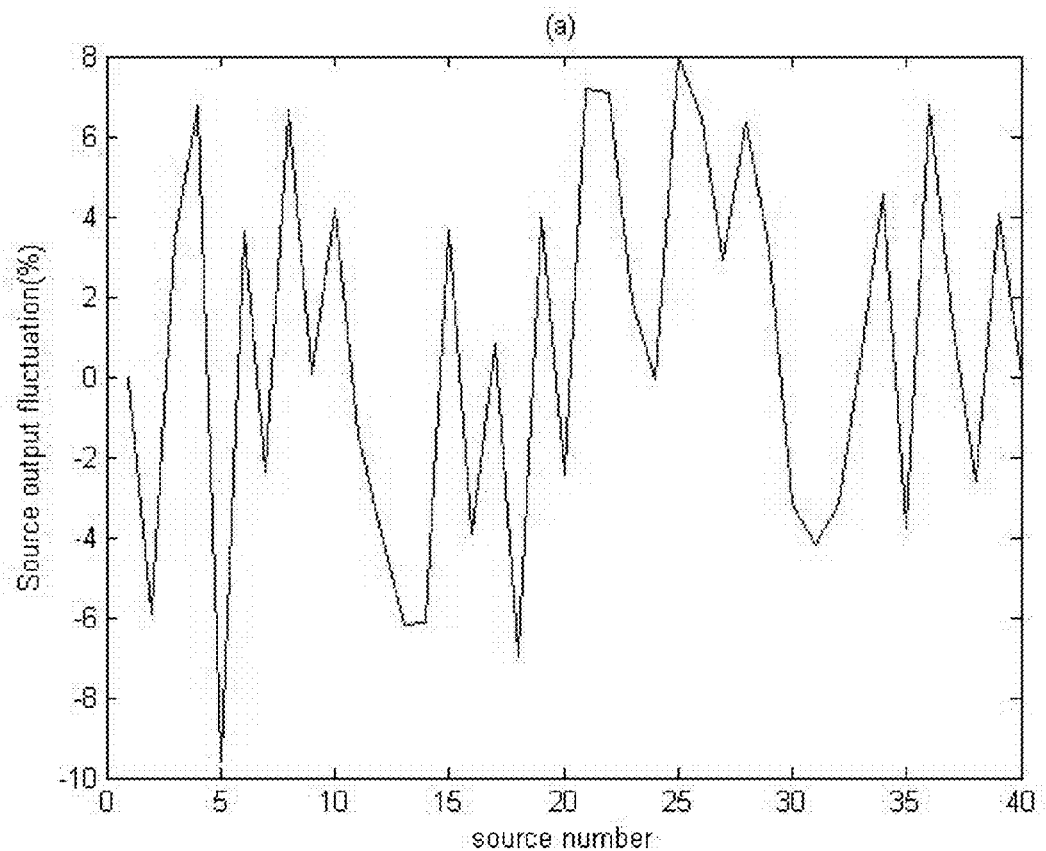
FIG. 10A shows the source output fluctuation of the IGCT reconstruction with noise data.
Figure 10B:
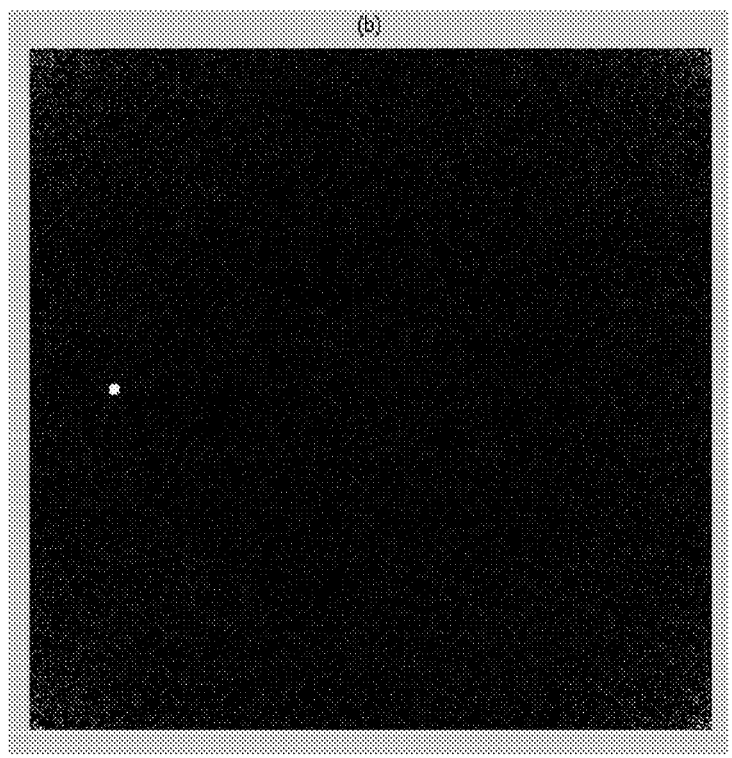
FIGS. 10B-C show the noise reconstruction without (FIG. 10B) and with (FIG. 10C) log($\alpha$) estimation.
Figure 10C:
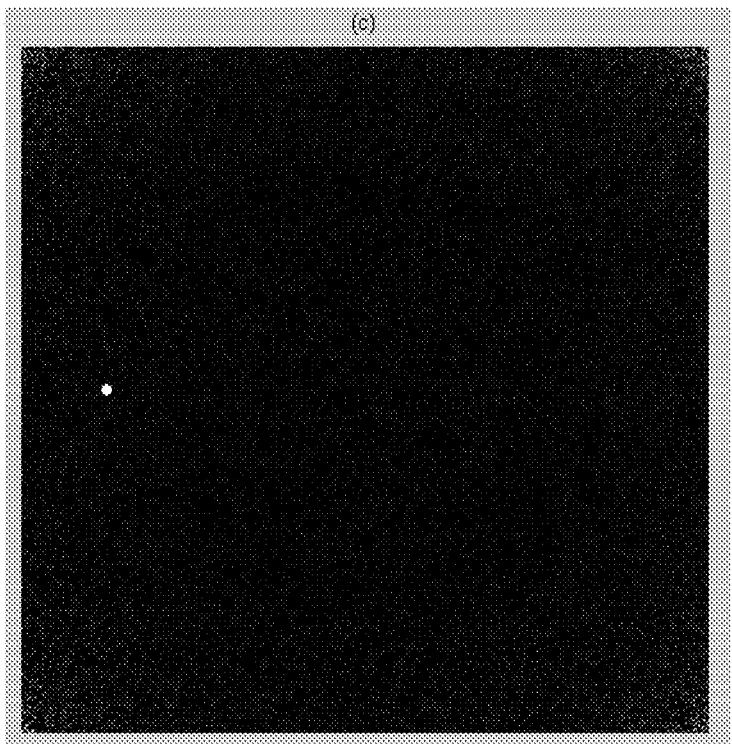
Figure 10D:
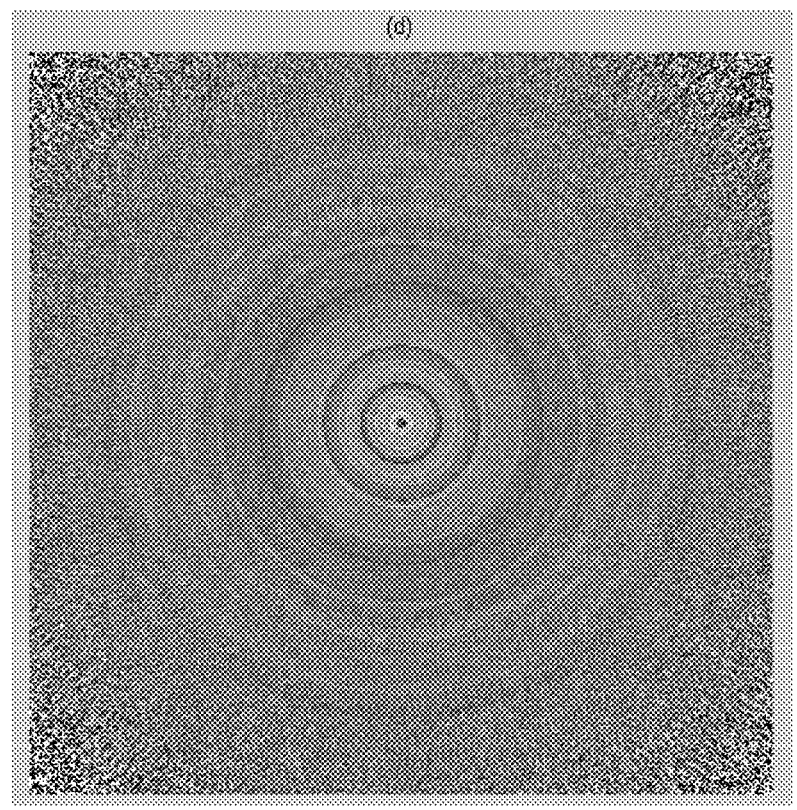
FIG. 10D shows the difference image between FIG. 10B and FIG. 10C.
Figure 10E:
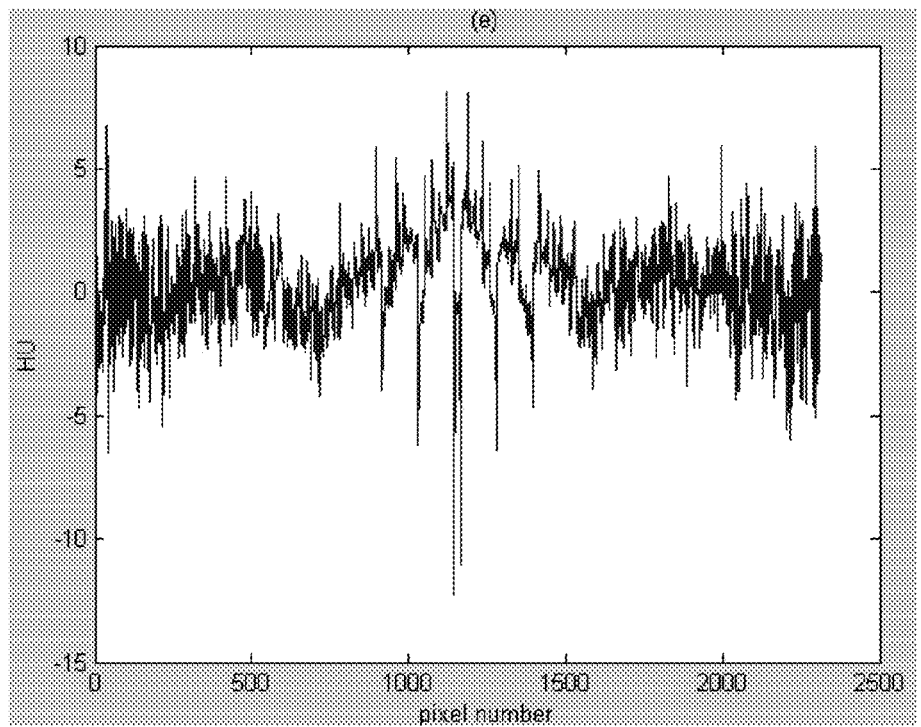
FIG. 10E shows the central profile through the difference image.

An off-centered 1 cm diameter water cylinder was reconstructed with and without $\log(\alpha)$ estimation. For the simulation, a nominal incident intensity of 3000 photons per ray was used. The actual intensity of the sources was different from source to source, but each source has the same intensity output over all views. This is probably a worst-case scenario for an IGCT system since the coherent errors cause ring-type artifacts. FIG. 10A shows the source output error of the IGCT reconstruction with noise data. FIGS. 10B-C show the noise reconstruction without (FIG. 10B) and with (FIG. 10C) log ($\alpha$) estimation and correction. The artifacts due to the source output errors can be seen by taking the difference between FIG. 10B and FIG. 10C. FIG. 10D shows the difference image between FIG. 10B and FIG. 10C. The artifacts level is shown in FIG. 10E, which shows the central profile through the difference image.

Examination of the Interpolation Error in the log($\alpha$) Estimation

When the estimation of log($\alpha$) is performed, it is assumed that the projection data for one source in the overlap region can be accurately estimated from the data for an already corrected source using interpolation. There could be interpolation errors, and these could cause image artifacts. The interpolation errors are expected to increase when the projection data varies rapidly in phi. In order to investigate the artifacts due to the interpolation error, the following steps were used.

By assuming no output fluctuation for all sources, log($\alpha$) estimation was performed. For the simulation, noiseless projection data of an off-centered object (to create variations in data as a function of phi) was used.

Examine the effect of interpolation error by taking difference between reconstructed images with and without log($\alpha$) estimation.

Figure 11A:
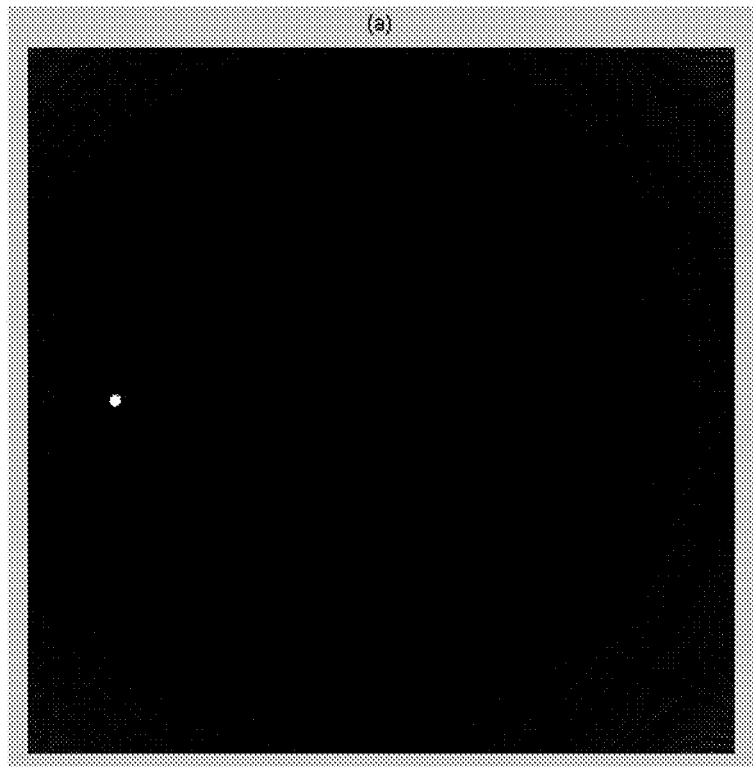
FIGS. 11A-B show the reconstructed image with (FIG. 11A) and without (FIG. 11B) log($\alpha$) estimation.
Figure 11B:
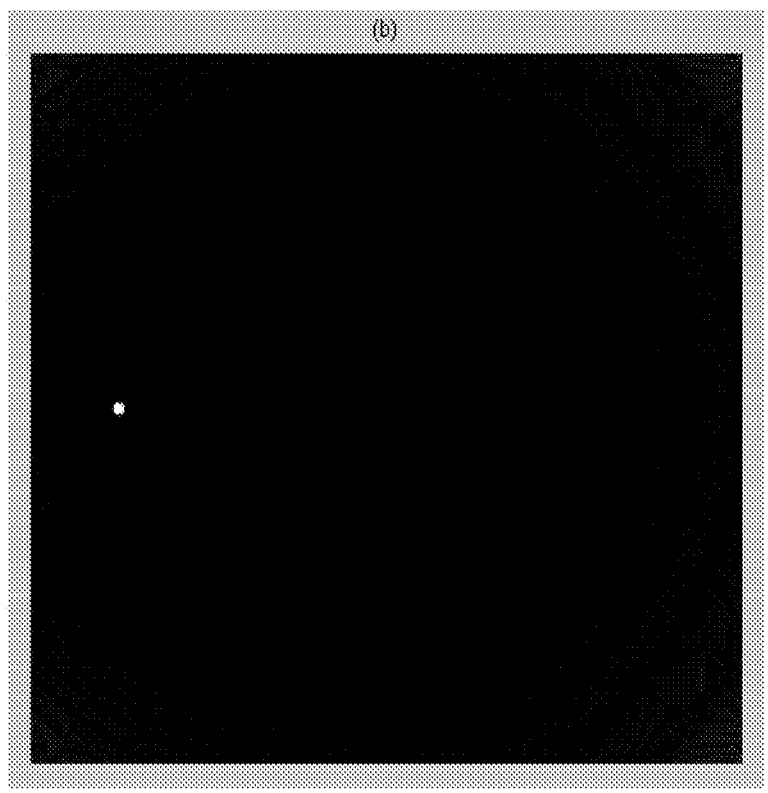
Figure 11C:
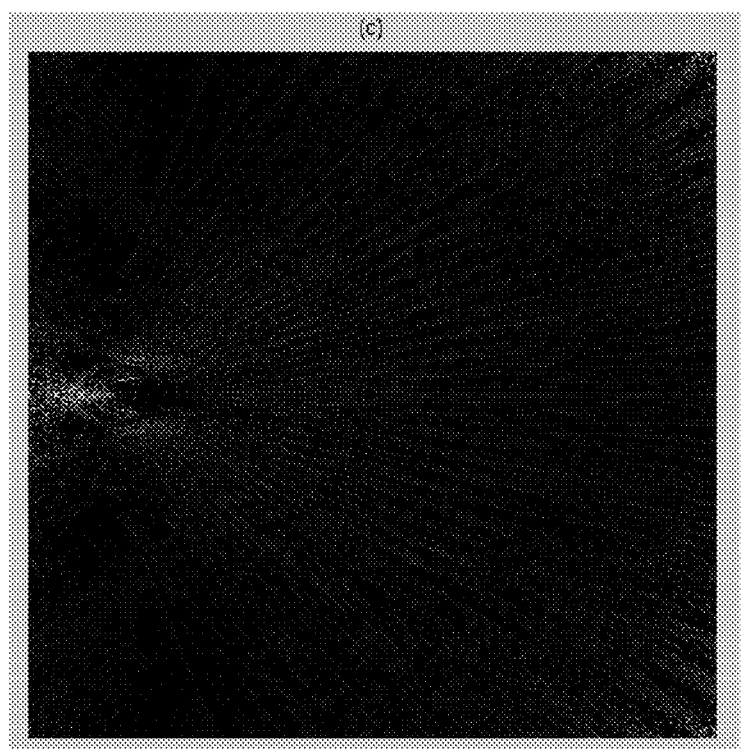
FIG. 11C shows the interpolation error image determined by the difference between the reconstructed images of FIG. 11A and FIG. 11B.
Figure 11D:
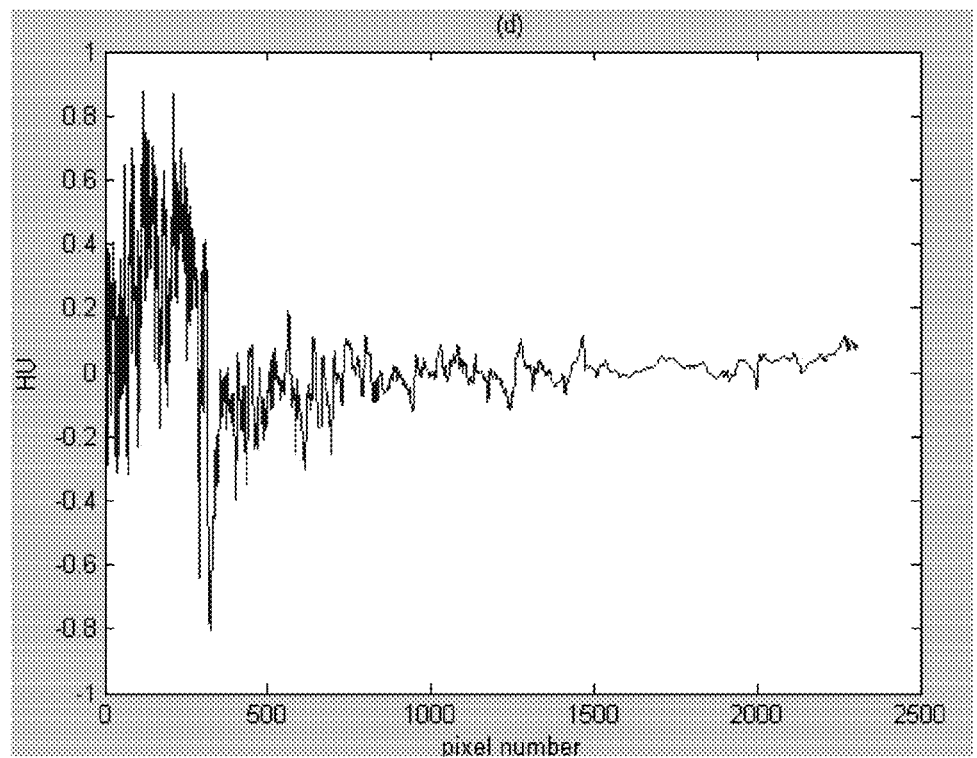
FIG. 11D is the central profile through the difference image
Figure 11E:
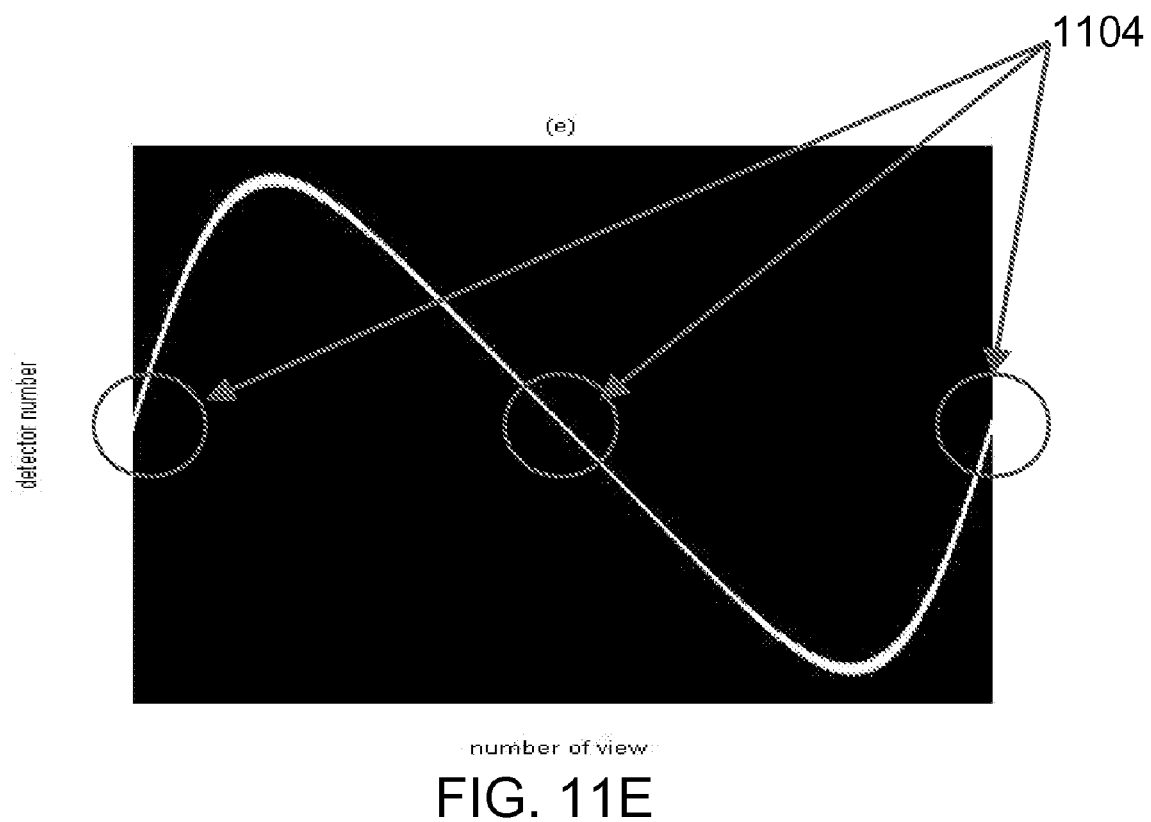
FIG. 11E shows a rebinned sonogram.

FIG. 11A-B show the reconstructed image with (FIG. 11A) and without (FIG. 11B) log($\alpha$) estimation. FIG. 11C shows the interpolation error image determined by the difference between the reconstructed images of FIG. 11A and FIG. 11B. FIG. 11D is the central profile through the difference image (FIG. 11C), and shows that the artifacts level due to the interpolation is below 1 HU. It is also observed that the horizontal direction of FIG. 11C shows higher artifacts level than the vertical direction. This can be understood by examining the rebinned sinogram, as shown in FIG. 11E. As can be seen in FIG. 11E, the portions 1104 in the sinogram that contain rapid variation in data as a function of phi correspond to the horizontal direction in FIG. 11C. Because the interpolation error is higher in these regions, reconstructed image has higher artifacts in the horizontal direction.

Discussion and Conclusions

Fluctuation of the source output has been shown to cause artifacts in the reconstructed image. Because all sources cannot see the reference channel in the multi-source IGCT system, an embodiment of the invention provides a new algorithm to estimate the source output fluctuation based on sources whose output is known, or which can be monitored using a reference channel. From the calculation of the noise variance ratio, we demonstrated the effect of the estimation error is negligible compared with that of the photon-counting statistics. The noise variance ratio can be further improved by increasing the number of overlapping detector channels between sources. The results show that the multi-source IGCT geometry that studied has enough overlap channels. Artifacts can be caused by interpolation errors and these are higher for objects that generate high frequency content in projection space, but with sufficient sampling the artifacts level can be made less than 1 HU.

Generalized Flow Chart

Figure 12:
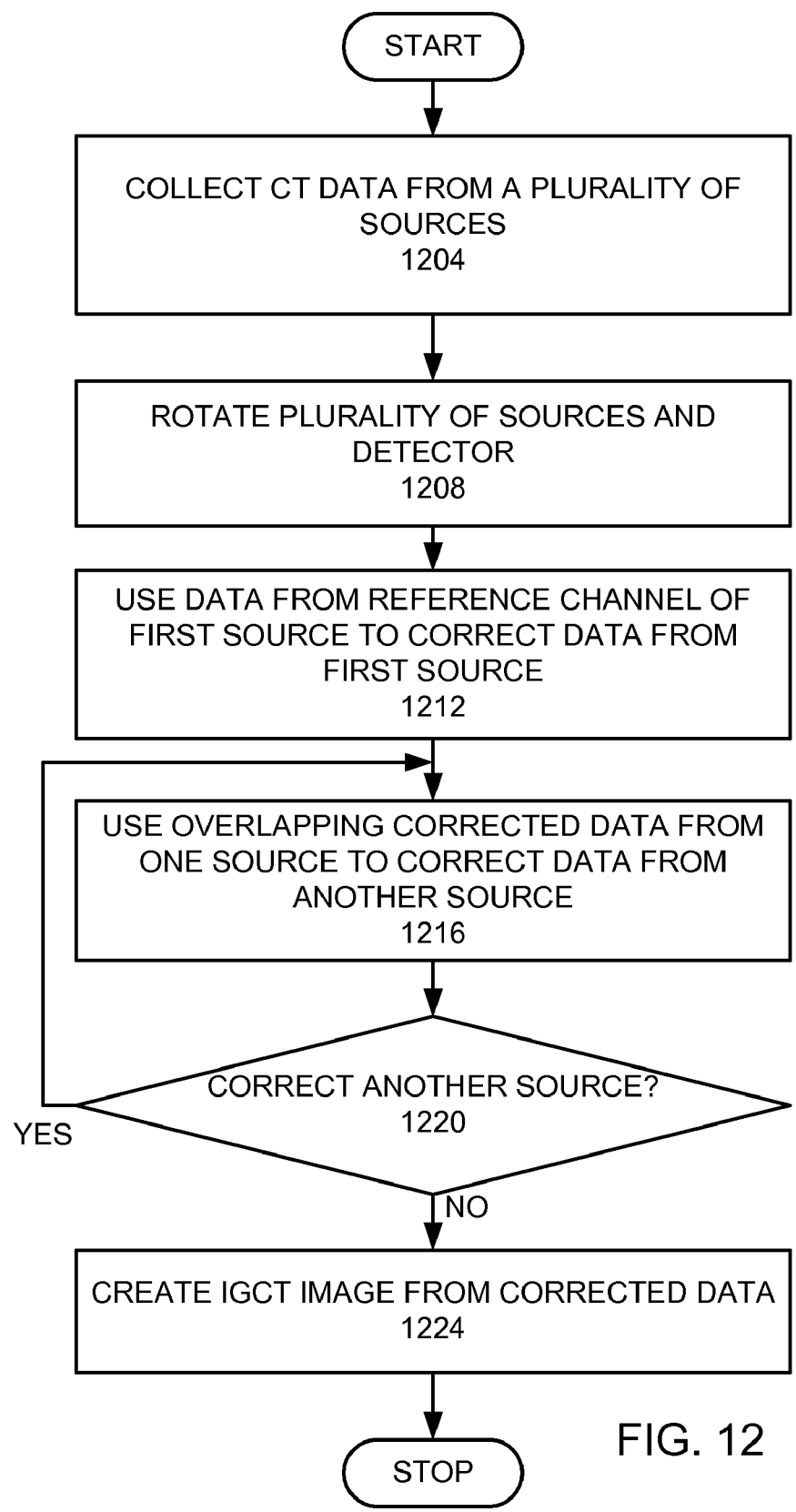
FIG. 12 is a flow chart of an embodiment of the invention.

This technique of normalizing the data in an inverse geometry computed tomography system may have various embodiments. A generalized flow chart is illustrated in FIG. 12. CT data is collected using a plurality of x-ray sources (step 1204). In an embodiment, the plurality of sources may have a first source with a reference channel, a second source without a reference channel, and possibly additional sources without a reference channel. Alternatively, the intensity of the first source may be known. The sources are placed in a configuration with a detector array to provide IGCT data. The plurality of sources and the detector array are rotated around an object to be imaged (step 1208). Data from the reference channel of the first source is used to correct the data from the first source (step 1212). This may be done by normalizing the data from the first source. If the intensity of the first source is known, this step can be skipped. Overlapping corrected data from one source is used to correct data from another source (step 1216). For example, a second source may have data that overlaps with data from the first source, in that at some time the first source is rotated to an angle that generated data that was also generated by the second source either previously or subsequently, and where the second source does not have a reference channel to provide data for normalization. The corrected data from the first source is used to estimate the intensity of the second source at this previous or subsequent angle and to correct the data from the second source, since there is data that overlaps. A determination is made on whether there is data from another source that needs to be corrected (step 1220). For example, if there is a third source without a reference channel that has uncorrected data that overlaps with data from the second source, the corrected data from the second source is used to correct data from the third source (step 1216). A determination is made on whether another source needs to be corrected (step 1220). This continues until the data needed for reconstruction has been corrected. The corrected data is then used to create an IGCT image (step 1224).

Figure 13A:
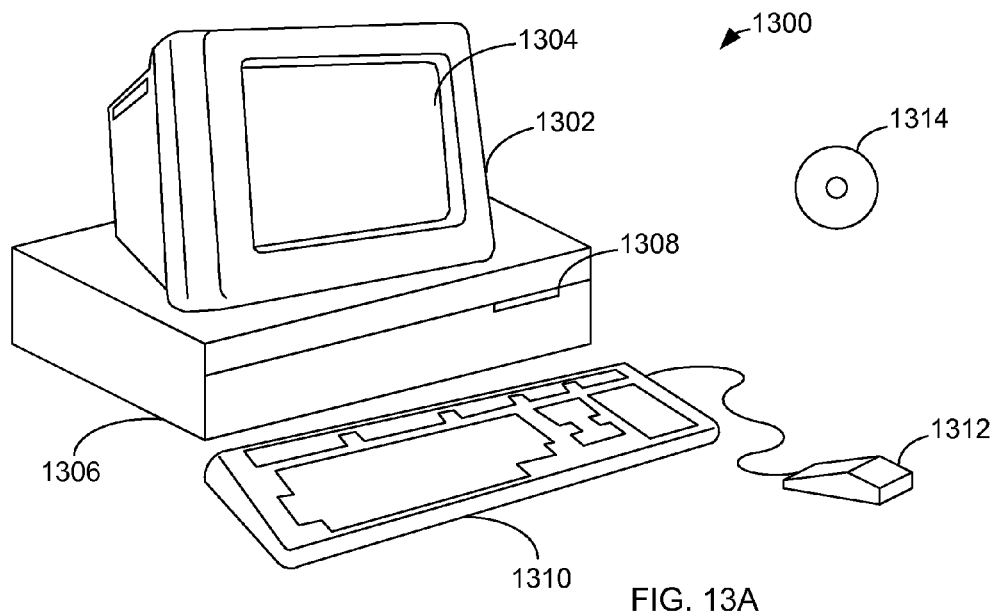
FIGS. 13A and 13B illustrate a computer system, which is suitable for controlling an IGCT system in embodiments of the present invention.
Figure 13B:
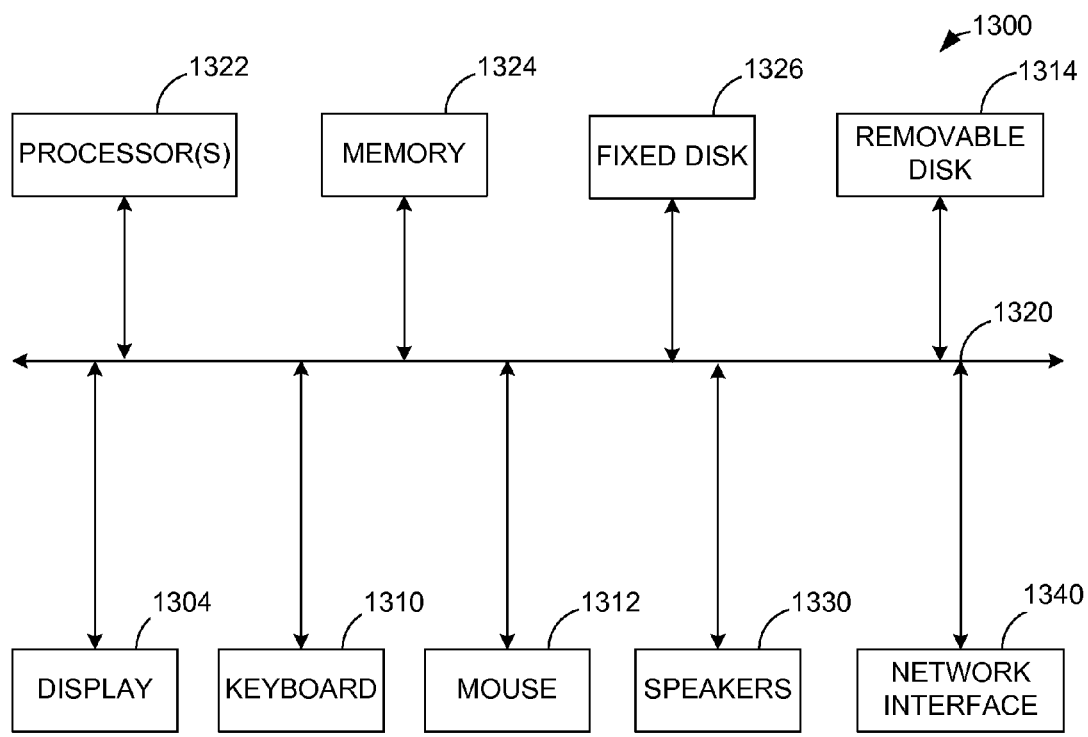

FIGS. 13A and 13B illustrate a computer system 1300, which is suitable for controlling an IGCT system in embodiments of the present invention. FIG. 13A shows one possible physical form of the computer system. Of course, the computer system may have many physical forms ranging from an integrated circuit, a printed circuit board, and a small handheld device up to a huge super computer. Computer system 1300 includes a monitor 1302, a display 1304, a housing 1306, a disk drive 1308, a keyboard 1310, and a mouse 1312. Disk 1314 is a computer-readable medium used to transfer data to and from computer system 1300.

FIG. 13B is an example of a block diagram for computer system 1300. Attached to system bus 1320 are a wide variety of subsystems. Processor(s) 1322 (also referred to as central processing units, or CPUs) are coupled to storage devices, including memory 1324. Memory 1324 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 1326 is also coupled bi-directionally to CPU 1322; it provides additional data storage capacity and may also include any of the computer-readable media described below. Fixed disk 1326 may be used to store programs, data, and the like and is typically a secondary storage medium (such as a hard disk) that is slower than primary storage. It will be appreciated that the information retained within fixed disk 1326 may, in appropriate cases, be incorporated in standard fashion as virtual memory in memory 1324. Removable disk 1314 may take the form of the computer-readable media described below.

CPU 1322 is also coupled to a variety of input/output devices, such as display 1304, keyboard 1310, mouse 1312, and speakers 1330. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 1322 optionally may be coupled to another computer or telecommunications network using network interface 1340. With such a network interface, it is contemplated that the CPU might receive information from the network, such as CT raw data, or might output information to the network, such as reconstructed images, in the course of performing the above-described method steps. Furthermore, method embodiments of the present invention may execute solely upon CPU 1322 or may execute over a network such as the Internet in conjunction with a remote CPU that shares a portion of the processing.

In addition, embodiments of the present invention further relate to computer storage products with a computer-readable medium that has computer code thereon for performing various computer-implemented operations. The media and computer code may be those specially designed and constructed for the purposes of the present invention, or they may be of the kind well known and available to those having skill in the computer software arts. Examples of tangible computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. For example, the IGCT system has been described as having multiple sources. These could be multiple sources in separate housings, multiple sources in the same housing, or multiple sources that are created by steering an electron beam over the surface of a target. All these types of multiple source systems are known in the art. It is therefore intended that the following appended claims be interpreted as including all such alterations, permutations, modifications, and various substitute equivalents as fall within the true spirit and scope of the present invention.

What is claimed is:

1. A method for imaging an object in a computed tomography (CT) system with a plurality of sources comprising a first source and a second source, wherein the plurality of sources together with a detector array are mounted on a rotatable gantry, and wherein an intensity of the second source has unknown fluctuations, comprising:
   a) collecting projection data using the first source in a first gantry position;
   b) collecting projection data using the second source in a second gantry position, wherein projection data from the first source in the first gantry position substantially overlaps projection data from the second source in the second gantry position; and
   c) using data from the first source at the first gantry position to correct for source fluctuations of the second source at the second gantry position.

2. The method of claim 1, wherein the using data from the first source at the first gantry position to correct for source fluctuations of the second source uses the projection data from the first source at the first gantry position that substantially overlaps with projection data from the second source to estimate the source fluctuation of the second source and further comprising using the source fluctuation to provide corrected data from the second source, wherein the corrected data from the second source is normalized.

3. The method, as recited in claim 2, wherein the plurality of sources further comprises a third source, wherein an intensity of the third source has unknown fluctuations, further comprising:
   d) collecting projection data using the third source in a third gantry position, wherein projection data from the second source in the second gantry position substantially overlaps projection data from the third source in the third gantry position; and
   e) using data from the second source at the second gantry position to correct for source fluctuations of the third source at the third gantry position.

4. The method of claim 3, wherein the using data from the second source at the second gantry position to correct for source fluctuations of the third source uses the projection data from the second source at the second gantry position that substantially overlaps with projection data from the third source to estimate the source fluctuation of the third source and further comprising using the source fluctuation to provide corrected data from the third source wherein the corrected data from the third source is normalized.

5. The method, as recited in claim 4, further comprising creating an inverse geometry computed tomography image from the corrected data.

6. The method, as recited in claim 5, further comprising displaying the inverse geometry computed tomography image.

7. The method, as recited in claim 6, wherein the first source has a reference channel and wherein the second source and the third source do not have a reference channel.

8. The method, as recited in claim 1, wherein the plurality of sources further comprises a third source, wherein the an intensity of the third source has unknown fluctuations, further comprising:
   d) collecting projection data using the third source in a third gantry position, wherein projection data from the second source in the second gantry position substantially overlaps projection data from the third source in the third gantry position; and
   e) using data from the second source at the second gantry position to correct for source fluctuations of the third source at the third gantry position.

9. The method, as recited in claim 1, further comprising creating an inverse geometry computed tomography image using the correction for source fluctuation.

10. The method, as recited in claim 9, further comprising displaying the inverse geometry computed tomography image.

11. The method, as recited in claim 10, wherein the first source has a reference channel and wherein the second source does not have a reference channel.

12. The method, as recited in claim 1, wherein the first source has a reference channel and wherein the second source does not have a reference channel.

13. A method for imaging an object in a computed tomography (CT) system comprising a plurality of sources and a detector array mounted on a rotatable gantry, wherein the plurality of sources comprise a source with a known intensity and at least one source with an intensity with an unknown fluctuation, comprising:
   a) collecting projection data from the source with a known intensity in a first gantry position;
   b) rotating the plurality of sources and a detector around the object to a second gantry position where the projection data from the source with known intensity in the first gantry position substantially overlaps with projection data from one source with an unknown fluctuation in the second gantry position; and c) using substantially overlapping projection data to estimate the unknown fluctuation and using the estimated unknown fluctuation to correct projection data from the one source with an unknown fluctuation in the second gantry position.

14. The method, as recited in claim 13, further comprising creating an inverse geometry computed tomography image from the corrected projection data.

15. The method, as recited in claim 14, further comprising displaying the inverse geometry computed tomography image.

16. The method, as recited in claim 15, wherein the corrected data is normalized.

17. The method, as recited in claim 16, wherein the source with a known intensity has a reference channel and the at least one source with an intensity with an unknown fluctuation does not have a reference channel.

18. An inverse geometry computed tomography apparatus for performing computed tomography on an object, comprising:
   a plurality of sources;
   a detector array;
   a frame on which the plurality of sources and detector array are mounted that allows the plurality of sources and detector array to be rotated around the object;
   a controller for controlling the frame, plurality of sources, and detector array, comprising
      at least one processor; and
      computer readable media coupled to the at least one processor, comprising:
         computer readable code for collecting projection data using a first source of the plurality of sources in a first gantry position;
         computer readable code for rotating the frame from the first gantry position to a second gantry position;
         computer readable code for collecting projection data using the second source in the second gantry position, wherein projection data from the first source in the first gantry position substantially overlaps projection data from the second source in the second gantry position;
         computer readable code for using data from the first source at the first gantry position to correct for source fluctuations of the second source at the second gantry position; and
         computer readable code for generating an image using the corrected source fluctuations.

19. The apparatus, as recited in claim 18, further comprising a display, wherein the computer readable media, further comprises computer readable code for displaying the image on the display.

* * * * *